(12) United States Patent
Chen et al.

(10) Patent No.: US 8,492,571 B2
(45) Date of Patent: Jul. 23, 2013

(54) MIXTURES OF AND METHODS OF USE FOR POLYUNSATURATED FATTY ACID-CONTAINING PHOSPHOLIPIDS AND ALKYL ETHER PHOSPHOLIPIDS SPECIES

(76) Inventors: Su Chen, Malta, NY (US); Hung Kwong, Malta, NY (US)

( * ) Notice: Subject to any disclaimer, the term of this patent is extended or adjusted under 35 U.S.C. 154(b) by 0 days.

(21) Appl. No.: 13/355,191

(22) Filed: Jan. 20, 2012

(65) Prior Publication Data

US 2012/0116104 A1      May 10, 2012

Related U.S. Application Data (63) Continuation of application No. 12/360,594, filed on Jan. 27, 2009, now abandoned, which is a continuation-in-part of application No. 11/458,451, filed on Jul. 19, 2006, now abandoned.

(51) Int. Cl.
  *C11B 1/00*  (2006.01)
  *A23J 7/00*  (2006.01)

(52) U.S. Cl.
  USPC .............................................. 554/18; 554/80

(58) Field of Classification Search
  USPC ...................................................... 554/18, 80
  See application file for complete search history.

(56) References Cited

U.S. PATENT DOCUMENTS

2004/0052837 A1*   3/2004   Stillwell et al. ............... 424/450

OTHER PUBLICATIONS

Chem. Abstr. of US Pub. 2004/0052837.*

* cited by examiner

*Primary Examiner* — Deborah D Carr
(74) *Attorney, Agent, or Firm* — Michael A. Blake (57) ABSTRACT

A chemical composition of a molecular species mixture of phospholipids, purified to at least 85% purity through chromatography purification, the chemical composition contains enriched both sn-1-acyl fatty chains/sn-2-docosahexaenoic acid molecular species and sn-1-ether fatty chains/sn-2-docosahexaenoic acid molecular species, the phospholipids are selected from the group consisting of: phosphatidylcholine, phosphatidylserine and phosphatidylethanolamine. Methods using the above disclosed composition in mammals to treat various conditions.

15 Claims, 3 Drawing Sheets

MIXTURES OF AND METHODS OF USE FOR POLYUNSATURATED FATTY ACID-CONTAINING PHOSPHOLIPIDS AND ALKYL ETHER PHOSPHOLIPIDS SPECIES

CROSS-REFERENCES

This patent application is a continuation of parent U.S. patent application Ser. No. 12/360,594 filed on Jan. 27, 2009 now abandoned by Su Chen, entitled "Mixtures of and Methods of Use for Polyunsaturated Fatty Acid-Containing Phospholipids and Alkyl Ether Phospholipids Species", the entire contents of which are fully incorporated by reference herein, and which parent patent application is a continuation-in-part of U.S. patent application Ser. No. 11/458,451 filed on Jul. 19, 2006 now abandoned by Su Chen, entitled "Mixtures of and Methods of Use for Polyunsaturated Fatty Acid-Containing Phospholipids and Alkyl Ether Phospholipids Species", the entire contents of which are also fully incorporated by reference herein.

FIELD OF THE INVENTION

The present invention relates to (1) the extraction and purification of new mixtures of phosphatidylcholine and alkyl ether phosphatidylcholine species as well as lysophosphatidylcholine species, which are obtained from the liver of saltwater fishes, with the structural characterization of (i) having a mixture of acyl and enriched alkyl fatty chains linked to the sn-1 position of the glycerol backbone, and (ii) having enriched ω-3 polyunsaturated fatty acid chains, in particular docosahexaenoic acid (DHA), linked to the sn-2 position or the sn-1 position of the glycerol backbone; (2) the preparation of disclosed mixtures of phosphatidylcholine, phosphatidylserine and phosphatidylethanolamine species as well as lysophosphatidylcholine, lysophosphatidylserine and lysophosphatidylethanolamine species from the phospholipid species mixtures extracted from the liver of saltwater fishes by enzymatic reactions; and (3) their use as carriers of ω-3-polyunsaturated fatty acids to the brain for the prevention and alleviation of neurodegenerative and neurological diseases which may be caused by the deficiency of ω-3 polyunsaturated fatty acids, in particular DHA.

BACKGROUND OF THE INVENTION

Omega-3 (or ω-3) polyunsaturated fatty acids, in particular docosahexaenoic acid (DHA), are especially important during prenatal brain development and maintenance of human brain function. Compared with saturated fatty acid, polyunsaturated fatty acid with multiple double bonds within molecule, in particular DHA, causes carbon-carbon chains to become more curved. The more kinked the fatty acid is, the more space it will take up, when it is built into cell membrane phospholipids, in order to keep neuronal membrane functions. This is the main reason that why the brain requires a large amount of nutritionally essential polyunsaturated fatty acids, especially DHA, because DHA and DHA-containing molecular species of phospholipids may contribute to important brain functions including signal transduction and information processing [Akbar et al., Docosahexaenoic acid: a positive modulator of Akt signaling in neuronal survival. Proc. Natl. Acad. Sci. U.S.A. 102: 10858 (2005)]. Alteration of neuronal membrane DHA-containing phospholipid species can not only influence crucial intracellular and intercellular signaling but also alter many membrane physical properties such as fluidity, phase transition temperature and bilayer thickness. The deficiency of DHA markedly affects neurotransmission, membrane-bound enzyme and ion channel activities leading to brain aging, Alzheimer's disease, Parkinson's disease, schizophrenia and peroxisomal disorders. For example, a study indicated that the concentration of DHA in patients with Alzheimer's disease is significantly decreased [Conquer, et al., Fatty acid analysis of blood plasma of patients with Alzheimer's disease, other type of dementia, and cognitive impairment, *Lipids,* 35:1305 (2000)]. The studies of Garcia et al. [Garcia et al., Effect of docosahexaenoic acid on the synthesis of phosphatidylserine in rat brain in microsomes and C6 gliome cells. *J. Neurochem.* 70: 24 (1998); Kim et al., Inhibition of neuronal apoptosis by docosahexaenoic acid (22:6n-3): Role of phosphatidylserine in anti-apoptotic effect. *J. Biol. Chem.* 275:35215 (2000)] found out the new role of DHA and phosphatidylserine in neuronal apoptosis, indicating that exogenous DHA may enhance phosphatidylserine accumulation in apoptotic Neuro-2A cells leading to the protection of neuronal cells from apoptotic death. The studies strongly suggest that one of supporting roles for anti-apoptosis of neurons is supplying DHA to the brain.

Because the human body cannot synthesize ω-3 polyunsaturated fatty acids, in particular DHA, exogenous introduction of DHA to human has been applied. There are a few products available for use as brain nutrients, such as fish oils (DHA-containing neutral lipids) and similar products.

Although these products contain DHA and other omega-3 polyunsaturated fatty acids, experiments have demonstrated that only a very small amount of DHA can be found in the brain after administering a large amount of these products. But an early study showed that DHA-containing lysophospholipid in albumin, rather than the forms of free DHA and other esterified DHA, is preferred in the uptake of DHA in the brain of young rats when an in vitro model of blood-brain barrier is used [Thies et al., Unsaturated fatty acids esterified in 2-acyl-1-lyso-phosphatidylcholine bound to albumin are more efficiently taken up by the young rat brain than unesterified form. *J. Neurochem.* 59: 1110 (1992)].

Interestingly, a study reported that dietary phospholipid with DHA-containing molecular species as supplementation is much more efficient than soybean phospholipid for ensuring a normal level DHA in the brain during the period of brain development in rats [Bourre and Dumont, *Neurosci. Lett.,* 335:129 (2002)] because DHA species are absent in the latter. The result suggests that DHA-containing phospholipid species are effective forms to be used as DHA carriers to brain.

Phosphatidylcholine (PC), phosphatidylserine (PS) and phosphatidylethanolamine (PE) as well as lysophosphatidylcholine (Lyso PC), lysophosphatidylserine (Lyso PS) and lysophosphatidyl-ethanolamine (Lyso PE) are naturally occurring phospholipid classes, existing in mixture forms of the molecular species. The structural diversity of the molecular species of phospholipids has been described in detail [Chen, *Lipids,* 32, 85 (1997); Chen et, al. *Biomed. Mass Spectrom.* 21, 655 (1992)]. Biochemical and biophysical functions of phospholipids are well documented and appear to be determined by the fatty acid composition of the lipids.

Ether phospholipids are usually found in animal tissues and human cells as minor components, existing together with molecular species of diacyl phospholipids carrying the same polar head group. It is well known that there are two predominant types of ether bonds in the phospholipid. One form is represented by the plasmalogens (with 1-alk-1'-enyl fatty chain linked to the sn-1 position of the glycerol backbone), which is the most abundant subclass of phospholipids in most tissues. The other form is alkyl phospholipids that contain 1-O-alkyl fatty chain(s) linked to the sn-1 position of the glycerol backbone. Although mixtures of phospholipids and ether phospholipids have been found in animals and humans [Diagne, et. al., Studies on ether phospholipids, *Biochim. Biophys. Acta*, 793, 221 (1984)], little has been described regarding the presence of phospholipid species mixtures containing 1-O-alkyl-2-DHA molecules, as well as DHA-containing lysophospholipids in aquatic animals.

Investigation of PC metabolism in human [Galli et al., Prolonged retention of doubly labeled phosphatidylcholine in human plasma and erythrocytes after oral administration. *Lipids*, 27: (1992)] indicated that a major portion of PC species can be found as intact molecules in plasma after oral administration of labeled phospholipid species. The result is supported by an animal experiment, suggesting that more than 80% of PC, which is recovered from the intestinal lymph of rats, is still intact after oral administration of phospholipids [Ikeda et al., Absorption and transport of base moieties of phosphatidylcholine and phosphatidylethanolamine in rats, *Biochim. Biophys. Acta*, 921; 245 (1987)].

However, fatty acid chains of phospholipids can be further hydrolyzed by lecithin-cholesterol acyltransferase in plasma after molecular species are incorporated into high density lipoprotein, and followed by phospholipase $A_1$ and phospholipase $A_2$ hydrolyses in the liver. Recently, several papers reported the possibility of transporting high density lipoprotein across the blood-brain barrier using an in vitro model [Balazs et al., Uptake and transport of high-density lipoprotein (HDL) and HDL-associated $\alpha$-tocopherol by an in vitro blood-brain barrier model. *J. Neurochem.* 89: 939 (2004)] and the importance of endothelial lipase in the metabolism of high density lipoprotein associated phospholipids at the blood-brain barrier [Ma et al., Endothelial lipase is a major genetic determinant for high-density lipoprotein concentration, structure, and metabolism. *Proc. Natl. Acad. Sci. U.S.A.* 100: 2748 (2003)], demonstrating that endothelial lipase (i) exhibits primarily the activity of phospholipase $A_1$ leading to the hydrolysis of sn-1 fatty acid chains from the molecular species of high density lipoprotein phospholipids, and (ii) is inactive in the hydrolysis of ether phospholipid molecular species [Gauster et al., Endothelial lipase release saturated and unsaturated fatty acid of high density lipoprotein phosphatidylcholine. *J. Lipid Res.* 46: 1517 (2005)].

An early study also showed that after the administration of lysophospholipids, these lipid species do not enhance fatty acid chain retention in mucosa and may survive from the hydrolysis of lecithin-cholesterol-acyltransferase in plasma, as well as other phospholipases in the liver [Viola et al., Absorption and distribution of arachidonate in rats receiving lysophospholipids by oral route, *J. Lipid Res.* 34, 1843 (1993)].

Based on these published results, it is clear to see that ether phospholipid species, such as 1-O-alkyl-2-acyl molecular species, and lysophospholipid molecular species are more stable in vivo lipid metabolism, compared with related acyl species. Because ether phospholipid and lysophospholipid species can be survived from blocking due to the hydrolysis of phospholipase $A_1$ and phospholipase $A_1$-like enzymes in vivo metabolism [Shamburek et al., Disappearance of two major phosphatidylcholine from plasma is predominantly via LCAT and hepatic lipase, *Am J. Physiol.* 271: E1073 (1996); Scagnelli, Plasma 1-palmitoyl-2-linoleoyl phosphatidylcholine. Evidence for extensive phospholipase $A_1$ hydrolysis and hepatic metabolism of the products, *J. Biol. Chem.* 266: 18002 (1991)], DHA-containing ether phospholipid species and DHA-containing lysophospholipid species can be delivered smoothly into the brain as carriers of DHA, resulting in the uptake of free DHA after brain phospholipase hydrolyses of the phospholipids species [Ross et al., Characterization of a novel phospholipase $A_2$ activity in human brain. *J. Neurochem.* 64, 2213 (1995)].

Interest is focused on the preparation of phospholipid species containing 1-O-alkyl-2-DHA molecules and DHA-containing lysophospholipid species. However, obtaining molecular species mixtures containing enriched DHA-containing ether phospholipids and -lysophospholipids species from aquatic animals is poorly understood [Chapelle, Plasmalogen and O-alkyl glycerophospholipids in aquatic animals, *Comp. Biochem. Physiol.* 88, 1 (1987)]. Additionally, the chemical synthesis of these phospholipids species is both difficult and expensive, and thus a large-scale preparation of the molecular species for use as potential brain health supplementation is not available. Thus there is a need for a method of a large-scale preparation of DHA-containing phospholipids and -lysophospholipids species for use as potential brain health supplementations.

SUMMARY OF THE INVENTION

The disclosed invention relates to a chemical composition of a molecular species mixture of phospholipids, purified to at least 85% purity through chromatography purification, the chemical composition contains enriched both sn-1-acyl fatty chains/sn-2-docosahexaenoic acid molecular species and sn-1-ether fatty chains/sn-2-docosahexaenoic acid molecular species, the phospholipids are selected from the group consisting of: phosphatidylcholine, phosphatidylserine and phosphatidylethanolamine.

The invention also relates to a process for preparing a composition of a molecular species mixture of phospholipids that contain enriched both sn-1-acyl fatty chains/sn-2-docosahexaenoic acid molecules and sn-1-ether fatty chains/sn-2-docosahexaenoic acid molecules, the process comprising: extracting phosphatidylcholine species mixtures from livers of saltwater fish; and purifying the phosphatidylcholine species mixtures to at least 85% purity by chromatography purification.

In addition, the invention relates to a process for preparing a composition of a molecular species mixture of phospholipids that contain enriched both sn-1-acyl fatty chains/sn-2-docosahexaenoic acid and sn-1-ether fatty chains/sn-2-docosahexaenoic acid molecules, the process comprising: transphosphatidylating a purified phosphatidylcholine species mixture into a phosphatidylserine species mixture, then purifying the phosphatidylserine species mixture to at least 85% purity by chromatography purification.

The invention also relates to a process for preparing a composition of a molecular species mixture of phospholipids that contain enriched both sn-1-acyl fatty chains/sn-2-docosahexaenoic acid and sn-1-ether fatty chains/sn-2-docosahexaenoic acid molecules, the process comprising: transphosphatidylating a purified phosphatidylcholine species mixture into a phosphatidylethanolamine species mixture; and purifying the phosphsphatidylethanolamine species mixture to at least 85% purity by chromatography purification.

The invention relates to a chemical composition of a molecular species mixture of lysophosphatidylcholine, purified to at least about 85% purity through chromatography purification, which contains enriched sn-1-docosahexaenoic acid molecules.

In addition, the invention relates to a process for preparing a composition of a molecular species mixture of lysophosphatidylcholine that contains the enriched sn-1-docosahexaenoic acid molecules, the process comprising: extracting lysophosphatidylcholine from a liver of a saltwater fish; and purifying the lysophosphatidylcholine to at least 85% purity by chromatography purification.

The invention also relates to a chemical composition of a molecular species mixture of phospholipids, purified to at least 90% purity through chromatography purification, the chemical composition contains sn-1-ether fatty chains/sn-2-docosaheaxnoic acid species only and does not contain sn-1-acyl fatty chains/sn-2-docosahexaenoic acid species, the phospholipids are selected from the group consisting of: phosphatidylcholine, phosphatidylserine and phosphatidylethanolamine.

In addition, the disclosed invention relates to a method of using the above disclosed mixtures in mammals to treat various conditions.

BRIEF DESCRIPTION OF THE DRAWINGS

The present disclosure will be better understood by those skilled in the pertinent art by referencing the accompanying drawings, where like elements are numbered alike in the several figures, in which.

DETAILED DESCRIPTION OF THE INVENTION

Surprisingly, the applicants have discovered that it is possible to obtain PC species mixtures with enriched 1-O-alkyl-2-DHA molecules and Lyso PC species mixtures with enriched DHA-containing molecule from the liver of saltwater fishes by chemical extraction, followed by column purification. For example, the PC species mixture from common dolphin liver contains approximately 50% of sn-2-(ω-3)-polyunsaturated fatty acid molecules, including approximately 25% of 1-O-alkyl-2-DHA molecules; for another example, the Lyso PC species mixture from shark liver contains approximately 33% of DHA-containing molecule. The collection of raw liver materials in a large quantity is readily available from marine animals.

A second aspect of the present invention is that it is possible to prepare disclosed mixtures of PS and PE species by the transphosphatidylation [Comfurius et, al. Enzymatic synthesis of phos-phatidylserine on small scale by use of a one-phase system, *J. Lipid Res.* 31, 1719 (1990)] using the special starting material combinations that consist of (i) phospholipase D, (ii) L-serine or ethanol-amine and (iii) the PC species mixtures extracted from the liver of saltwater fishes.

A third aspect of the present invention relates to the preparation of disclosed sn-2-DHA-Lyso PC, -Lyso PS and -Lyso PE species mixtures by lipase hydrolyses of mixtures of the liver PC species, as well as transphosphatidylated fish liver-PS and -PE species [Slotboom et al., Hydrolysis of phosphoglycerides by Purified lipase preparations II. Preparation of unsaturated 2-monoacyl choline phosphoglycerides, *Chem. Phys. Lipids*, 4, 30 (1970)].

A fourth aspect of the present invention is involved in the preparation of disclosed mixtures of 1-O-alkyl-2-DHA-PC, -PS and -PE species using 1-O-alkyl-2-hydroxy-PC species mixtures [Paltauf et al., In *Method in Enzymology*, 197, 141 (1991)] as the starting material, which are prepared from the liver PC species and/or the liver Lyso PC species mixtures.

Compared with available phospholipid product Lecithin that contains soybean PC species mixtures, newly discovered and purified PC and Lyso PC species mixtures are alternative supplementations. Furthermore, the PC and Lyso PC may be used as brain nutrients for the delay of brain aging. However, Lecithin containing PC species mixtures lack DHA molecular species.

A mixture of bovine cortex phosphatidylserine (BCPS) species, which contains approximately 8% of sn-2-DHA molecular species, was registered as a drug in Europe for both cognitive deficits in the old and the alleviation of Alzheimer's disease [Crook et al., Effect of phosphatidyl-serine in Alzheimer's Disease, *Psychopharmacology Bulletin* 28, 61 (1992); Pepeu, et al., A review of phosphatidylserine pharmaceutical and clinical effects: Is phosphatidylserine a drug for ageing brain? *Pharmacol. Res.* 33, 51 (1996)]. Unfortunately, the risk of bovine spongiform encephalopathy made the use of the BCPS extracted from bovine brain potentially dangerous.

Compared with the BCPS, disclosed mixtures of transphosphatidylated fish liver-PS and -PE species, as well as sn-2-DHA-Lyso PS and -Lyso PE and alkyl-DHA-PC, -PS and -PE species contain much more sn-2-DHA molecular species (over 40%, even 100%), and are considered to be of much more therapeutic interest in the alleviation and treatment of neurodegenerative and neurological diseases, which are associated with dysfunctions of neurotrophins and neurotrophin receptors caused by the deficiency of (ω-3) polyunsaturated fatty acids, in particular DHA.

Compared with commercially available phospholipids product transphosphatidylated soybean PS species mixtures, disclosed phospholipid species mixtures are qualified for use as substitutes of the BCPS for the treatment of neurodegenerative and neurological diseases caused by DHA deficiency, because DHA-containing phospholipid species are absent in currently available transphosphatidylated soybean PS species mixtures (http://www.cfsan.fda.gov/~dms/ds-ltr36.html).

Although the preparation of a mixture of transphosphatidylated fish brain-PS species has been reported (European patent: EPO 819 760 A1), the disadvantages of the preparation include: (i) the collection of fish brain material in a large quantity is difficult, and thus the product preparation in industrial scale is limited; (ii) Lyso PC has less than 5% of fish brain phospholipids, and DHA-containing Lyso PC is almost absent; and (iii) 1-O-alkyl-DHA phospholipids species are almost absent in fish brain.

Although the preparation of a mixture of transphosphatidylated fish skin-PS has been also reported, [Hosokawa et al., Conversion to docosahexaenoic acid-containing phosphatidylserine from squid skin lecithin by phospholipase D-mediated transphosphatidylation, *J. Agric. Food. Chem.* 48, 4550 (2000)], the collection of fish skin as starting materials in a large quantity is much more difficult, and thus an industrial scale preparation of the product is almost impossible. Furthermore, 1-O-alkyl-DHA phospholipids species and DHA-containing lysophospholipids are almost absent in fish skin as well.

Materials and procedures described in this disclosure have made it possible to prepare a series of disclosed mixtures of phospholipid species in a large scale, and even in an industrial scale. The resulting products can be used as the preventive and therapeutic reagents for brain and mental health.

Example 1

Preparation of Crude Lipids Extracted from the Liver of Saltwater Fishes

About two sharks were obtained in a fish market near the city of Medan in Indonesia, and the livers (approximately

Figure 1:
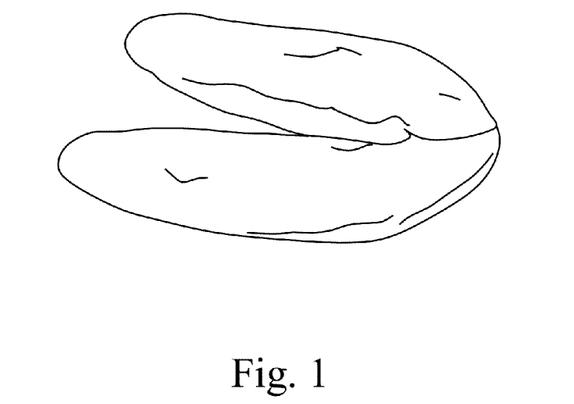
FIG. 1 is a top view of a shark liver.

1,170 grams (FIG. 1; see below) and 550 grams of the wet liver material, respectively) were transported in ice and then passed through a hand meat grinder. Tiny liver fragments were made with an electronic blender and were then mixed with about 20 volumes of cold acetone standing for four hours. After removing the acetone, the liver fragments, now the pellets were dried under nitrogen, and then the dried pellets were homogenized with about 10 volumes (w/v) of ethanol/ethyl acetate (1/1; v/v) stirring overnight. After evaporation of the ethanol/ethyl acetate, about 172 grams of crude lipids extracted from 1,170 grams of the wet liver material were obtained.

Figure 2:
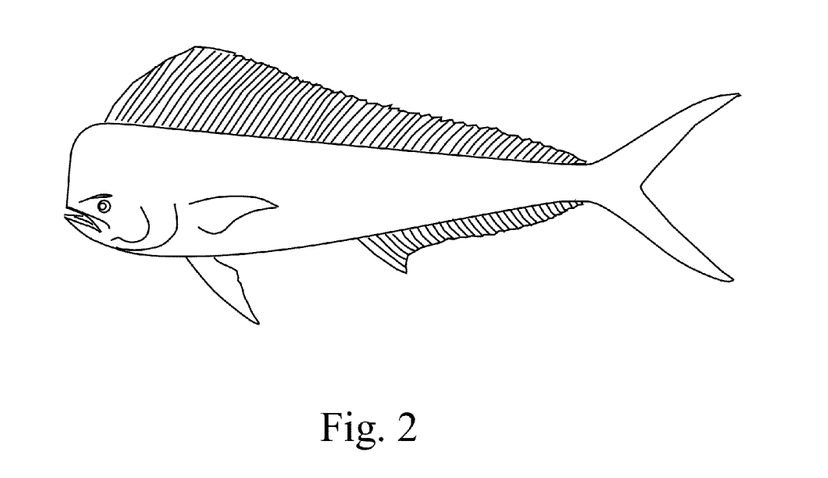
FIG. 2 is a top view of a common dolphin fish (*coryphaena hippurus*)

About 50 grams of the crude lipids were mixed with about 10 volumes (w/v) of acetone, and then the solution was stirred at about 30° C. for about 90 min. The mixture was filtered, and the acetone extract was kept at about −20° C. for overnight. The mixture solution was rapidly filtered and led to the precipitation of crude phospholipids (approximately 23.4 grams), consisting of about 80% of PC, about 15% of Lyso PC and about 5% of PE and others. The crude lipids and phospholipids are also harvested from the livers of frozen common dolphin (FIG. 2; about 770 gram s of the wet liver material), tuna (about 720 grams of the wet liver material) and salmon (about 810 grams of the wet liver material), which were provided by a Fishing Company located in the province of Fujian in China, using the procedure described above.

Example 2

Purification of PC and Lyso PC from Crude Phospholipids

Mixtures of PC and Lyso PC species were purified from about 10 grams of crude phospholipids by silica gel chromatography using an axial pressure in an about 250 mL-column equilibrated with chloroform/methanol (95/5); gradient elution was performed with mixtures of chloroform/methanol 90/10 (v/v), 80/20 (v/v), 70/30 (v/v), and 60/40 (v/v). PC species mixture was eluted from the column with a mixture of chloroform/methanol/water 50/50/1 (v/v/v), monitored by thin layer chromatography (TLC); and Lyso PC species mixture was eluted from the column with a mixture of chloroform/methanol/water 50/50/5 (v/v/v), monitored by TLC. The structures and percentage of purified PC and Lyso PC species mixtures, which were obtained by intensities of their protonated molecules of mass spectrometry [Brugger et al., Proc. Natl. Acad. Sci. USA, 94, 2339 (1997); Liebisch et al., Clin. Chem. 48, 2217 (2002)], are shown below.

(sn-1 position) $CH_2-COOC_{15}H_{31}, COOC_{16}H_{33}, COOC_{17}H_{35}, OC_{16}H_{33}, OC_{18}H_{37}, OC_{18}H_{35}$ (sn-2 position) $CH-\Big\langle COOC_{13}H_{27}, COOC_{15}H_{31}, COOC_{15}H_{29}, COOC_{17}H_{33}$
$COOC_{19}H_{29}(EPA), COOC_{19}H_{31}, COOC_{21}H_{33}, COOC_{21}H_{31}(DHA)$ (sn-3 position) $CH_2-O-\underset{OH}{\overset{O}{\underset{\|}{P}}}-O-CH_2-CH_2-\underset{CH_3}{\overset{CH_3}{N^+}}-CH_3$ [PC]

| $[M + H]^+$ | Molecular Species* | Dolphin (%) | Shark (%) | Tuna (%) | Salmon (%) |
|---|---|---|---|---|---|
| 834.6 | 18:0-22:6 | 2.6 ± 0.5** | 7.4 ± 2.0 | 7.7 ± 1.1 | 4.7 ± 0.2 |
| 822.6 | aa18:0-22:5*** | 3.4 ± 0.3 | 2.8 ± 0.3 | 2.9 ± 0.7 | 2.7 ± 0.6 |
| 820.6 | 17:0-22:6 | 9.6 ± 1.1 | 7.8 ± 2.3 | 3.9 ± 0.3 | 4.7 ± 0.4 |
| 818.6 | aa18:1-22:6 | 7.2 ± 1.7 | 6.9 ± 1.7 | 3.6 ± 0.7 | 2.3 ± 0.2 |
| 806.6 | 16:0-22:6 | 12.6 ± 2.2 | 15.9 ± 3.3 | 19.7 ± 2.7 | 13.9 ± 2.3 |
| 794.6 | aa18:1-20:4 aa16:0-22:5 | 3.5 ± 0.7 | 3.9 ± 1.1 | 2.7 ± 0.5 | 3.0 ± 0.8 |
| 792.6 | aa16:0-22:6 aa18:1-20:5 | 17.3 ± 2.1 | 9.8 ± 1.2 | 4.2 ± 1.2 | 12.5 ± 1.7 |
| 782.6 | 16:0-20:4 | 4.0 ± 0.6 | 4.8 ± 1.1 | 7.3 ± 0.3 | 4.8 ± 1.1 |
| 780.6 | 16:0-20:5 | 5.9 ± 1.1 | 2.8 ± 0.5 | 4.2 ± 0.8 | 7.0 ± 1.6 |
| 760.6 | 16:0-18:1 | 9.4 ± 2.0 | 7.8 ± 1.0 | 12.1 ± 2.5 | 11.2 ± 2.1 |
| 746.6 | aa16:0-18:1 | 2.5 ± 0.7 | 9.9 ± 1.6 | 6.3 ± 1.1 | 3.3 ± 0.3 |
| 734.6 | 16:0-16:0 | 11 ± 1.7 | 9.2 ± 1.8 | 12.8 ± 1.9 | 13.9 ± 3.1 |
| 732.6 | 16:0-16:1 | 3.1 ± 0.6 | 3.0 ± 1.7 | 3.2 ± 0.5 | 3.7 ± 1.1 |
| 720.6 | aa16:0-16:0 | 3.2 ± 1.1 | 2.6 ± 0.2 | 3.9 ± 0.8 | 3.4 ± 0.9 |
| 718.6 | aa16:0-16:1 | 1.2 ± 0.3 | 2.1 ± 1.1 | 2.6 ± 0.4 | 1.4 ± 0.7 |
| 706.6 | 16:0-14:0 | 3.3 ± 1.5 | 3.2 ± 1.3 | 3.6 ± 1.1 | 7.6 ± 1.4 |
| Total ω-3 fatty acid species | | 55.2 | 50.6 | 43.3 | 45 |
| Total DHA species | | 49.3 | 47.8 | 39 | 38 |
| Total acylalkyl DHA species | | 24.5 | 16.7 | 7.8 | 14.8 |
| Total acylalkyl species | | 38.3 | 37.9 | 26 | 28.6 |

*X:Y-x:y (For example 16:0-22:6), where X is the total carbon number of fatty acids esterified at sn-1 position, and Y is the total unsaturation degrees of the fatty acid groups; where x is the total carbon number of fatty acids esterified at sn-2 position, and y is the total unsaturation degrees of the fatty acid groups (Chen, Lipids, 32, 85 (1997)).
**Semiquantitative results were generated from the intensity average of protonated molecules ([M + H]$^+$) of the molecular species of the liver PCs, based on three replicate experiments of mass spectrometry.
***aa16:0-22:5 is alkylacyl PC species

| $[M + H]^+$ | Molecular Species | Dolphin (%) | Shark (%) | Tuna (%) |
|---|---|---|---|---|
| 568.5 | 22:6 | 31.1 ± 1.3 | 33.3 ± 1.6 | 23.9 ± 1.4 |
| 544.5 | 20:4 | 7.8 ± 0.3 | 8.5 ± 0.9 | 9.5 ± 0.1 |
| 542.5 | 20:5 | 8.1 ± 0.7 | 8.0 ± 0.7 | 3.4 ± 0.3 |
| 524.5 | 18:0 | 6.4 ± 0.3 | 6.8 ± 0.7 | 13.8 ± 0.3 |
| 522.5 | 18:1 | 12.5 ± 0.6 | 11.9 ± 0.8 | 7.2 ± 0.3 |
| 510.5 | a18:0* | 2.0 ± 0.4 | 2.1 ± 0.5 | 3.6 ± 0.2 |
| 508.5 | a18:1 | 3.0 ± 0.2 | 3.1 ± 0.3 | 2.5 ± 0.2 |
| 496.5 | 16:0 | 23.3 ± 1.7 | 21.4 ± 1.5 | 29.4 ± 2.5 |
| 482.5 | a16:0 | 2.3 ± 0.2 | 1.9 ± 0.8 | 3.5 ± 0.4 |
| -continued |
| $[M + H]^+$ | Molecular Species | Dolphin (%) | Shark (%) | Tuna (%) |
| 480.5 | a16:1 | 0.4 ± 0.04 | 1.3 ± 0.1 | 1.2 ± 0.3 |
| 468.5 | 14:0 | 2.8 ± 0.2 | 2.5 ± 0.8 | 1.7 ± 0.7 |
| 454.5 | a14:0 | 0.3 ± 0.1 | 1.3 ± 0.06 | 0.5 ± 0.3 |
| Total Alkyl species | | 7.7 | 7.6 | 10.6 |
| Total DHA species | | 31.1 | 33.3 | 23.9 |

*a18:0 is alkyl chain at the sn-1 position

Example 3

Preparation of Mixtures of Transphosphatidylated-Fish Liver PS Species

About 4 mL of acetate buffer (0.2M; pH 5.5), containing about 40 mM of calcium chloride and two grams of L-serine, were prepared at about 45° C. and then placed into an 20-mL disposable vial containing about 400 mg of purified PC from shark liver or about 450 mg of crude phospholipids. The vial was generally fully filled with argon. The enzymatic reaction was started by adding about 10 Units of phospholipse D (*Streptomyces* sp, BIOMOL, Plymouth Meeting, Pa., U.S.A). The mixture was left to react for about 15 hours at about 45° C. on a shaker. Once the reaction was complete, the vial was unloaded with about 40 mL of a mixture of chloroform/methanol 2/1 (v/v) and about 4 mL of water. The two separated phases were formed, and PS was in the down-phase. PS remaining in the up-phase was re-extracted with chloroform. After drying the combined two organic phases, PS was purified by silica chromatography, as described in Example 2, with an about 250 mL-column. PS was eluted with a mixture of chloroform/methanol 55/45 (v/v). About 285 mg of the product were obtained after purification. PS species mixture was also made from the PC species mixture of common dolphin liver, as described above. Structures of the PS products are shown below. The molecular species were identified by negative-ion electrospray mass spectrometry.

Example 4

Preparation of Mixtures of Transphosphatidylated-Fish Liver PE Species

About 4 mL of acetate buffer (0.2M; pH 5.5), containing about 40 mM of calcium chloride and about 800 mg of ethanolamine were prepared in an about 20-mL disposable vial at room temperature, and then the pH of the solution was adjusted to about pH 5.5 with glacial acetic acid. About 400 mg of purified PC from shark liver or about 450 mg of crude phospholipids were added. The vial was generally fully filled with argon. The enzymatic reaction was started by adding about 10 Units of phospholipse D (*Streptomyces* sp, BIO-MOL, Plymouth Meeting, Pa., USA). The mixture was left to react for about 15 hours at about 45° C. on a shaker. Once the reaction was complete, the vial was unloaded with about 40 mL of a mixture of chloroform/methanol 2/1 (v/v) and about 4 mL of water. The two separated phases were formed, and PE was in the down-phase. PE remaining in the up-phase was re-extracted with chloroform. After drying the combined two ture from salmon liver, as described above. Structures of the PE products are shown below.

Example 5

Preparation of Mixtures of sn-2-acyl Lyso PC Species

About 200 mg of the PC species mixture extracted from the liver were dissolved in about 10 mL of a Tris buffer (100 mM; pH 6.5) in the presence of about 50 mM of calcium chloride, about 200 µl of 30% of bovine albumin solution and about 70 mg of sodium deoxycholate, and then the mixture was sonicated at about 4° C. The enzymatic reaction was started by adding about 35 mg of lipase (*Rhizopus arrhizus*; SIGMA, St. Louis, Mo., USA). The mixture was left to react for about 3 hours at 30° C. on a shaker. Once the reaction was complete, the vial was unloaded with about 50 mL of a mixture of chloroform/methanol 2/1 (v/v). The two separated phases were formed, and Lyso PC is in the down-phase. Lyso PC remaining in the up-phase was re-extracted with chloroform. After drying the combined two organic phases, silica chromatography (using a 150 mL-column) was used to purify Lyso PC. The product was eluted with a mixture of chloroform/methanol 50/50/2 (v/v/v). Approximately 132 mg of the product was obtained after purification. Structures and percentages of the Lyso PC species, which are tentatively analyzed by intensities of their protonated molecules of electrospray mass spectrometry, are shown below.

| $[M + H]^+$ | Molecular Species | Shark (%) |
|---|---|---|
| 570.5 | 22:5 | 10 ± 0.35 |
| 568.5 | 22:6 | 48 ± 2.5 |
| 544.5 | 20:4 | 15 ± 0.55 |
| 542.5 | 20:5 | 14 ± 1.25 |
| 522.5 | 18:1 | 6.0 ± 0.75 |
| 496.5 | 16:0 | 6.9 ± 0.45 |
| Total ω-3 fatty acid species | | 62 |

Example 6

Preparation of Mixtures of sn-2-acyl-Lyso PS and -Lyso PE Species

About 200 mg of transphosphatidylated-fish liver-PS were dissolved in about 10 mL of a Tris buffer (100 mM; pH 6.5) in the presence of about 50 mM of calcium chloride, about 200 µl of about 30% of bovine albumin solution and about 70 mg of sodium deoxycholate, and then the mixture was sonicated at about 4° C. After adding about 35 mg of lipase (Rhizopus arrhizus; SIGMA, St. Louis, Mo., USA), the vail was fully filled with argon. The mixture was left to react for about 3 hours at about 30° C. on a shaker. Once the reaction was complete, the vial was unloaded with about 50 mL of a mixture of chloroform/methanol 2/1 (v/v). The two phases were allowed to separate, and Lyso PS is in the down-phase. Lyso PS remaining in the up-phase was re-extracted with chloroform. After drying the combined two organic phases, silica chromatography (using a 150 mL-column) was used to purify Lyso PS. The product was eluted with a mixture of chloroform/methanol 45/55 (v/v). The Lyso PE species mixture was also prepared from transphosphatidylated-fish liver-PE as described above, and was eluted with chloroform/methanol 55/45 (v/v). Structures of the two mixtures are shown below. The molecular species were identified by negative-ion electrospray mass spectrometry.

Example 7

Preparation of a Mixture of 1-O-alkyl-2-hydroxyl-Phosphatidylcholine Species

Approximately 500 mg of dried crude phospholipids extracted from shark liver were dissolved with about 18 mL of methanol, and then about 2 mL of 5M NaOH were added. The mixture was left to react at room temperature for overnight (more than about 15 hours). The lipids in reacted solution were extracted by adding about 22 mL of methanol, about 40 mL of chloroform and about 34 mL of water. After removing the up-phase, another about 2 mL of chloroform were added, and the solution was left at about −20° C. for several hours. The clear solution was taken out, and the mixture of 1-O-alkyl-2-hydroxy-phosphatidylcholine species was purified with silica column (a 150 mL-column) as described in Example 5. The product was eluted with a mixture of chloroform/methanol/water (50/50/2). About 97 mg of the product were obtained. Structures of the mixture of 1-O-alkyl-2-hydroxy-phosphatidylcholine species are shown below.

Example 8

Preparation of Mixture of 1-O-alkyl-2-DHA-Phosphatidylcholine Species

About 70 mg of 1-O-alkyl-2-hydroxyl PC species mixture, about 100 mg of DHA (SIGMA, St. Louis, Mo., USA), about 160 mg of dicyclohexylcarbodiimide (SIGMA, St. Louis, Mo., USA) and about 240 mg of 4-dimethylaminopyridine (SIGMA, St. Louis, Mo., USA) were dissolved in 3 mL of chloroform (HPLC grade). The vial was generally fully filled with argon and then put into another container that was generally fully filled with nitrogen. It was left to react at about 40° C. for about 20 hours. About one mL of chloroform was added, and the reaction mixture was then applied to a 150-mL silica column equilibrated with chloroform/methanol 95/5 (v/v). The PC product was eluted with a mixture of chloroform/methanol 50/50 (v/v). Structures (shown as below) of the product were identified by mass spectrometry as O-14:0/22:6 PC ([M+H]$^+$ 764.6; 9%). 0-16:1/22:6 PC ([M+H]$^+$ 790.6; 18%), 0-16:0/22:6 PC ([M+H]$^+$ 792.6; 25%), 0-18:1/22:6 PC ([M+H]$^+$ 818.6; 33%) and O-18:0/22:6 PC ([M+H]$^+$ 820.7; 15%).

Example 9

Preparation of Mixtures of 1-O-alkyl-2-DHA-PS and -PE Species

About 1 mL of acetate buffer (0.2M; pH 5.5), containing about 40 mM of calcium chloride and about 500 mg of L-serine was prepared in a 20-mL disposable vial at about 45° C. About 15 mg of 1-O-alkyl-DHA-PC species mixture were added to the vial generally fully filled with argon. The enzymatic reaction was started by adding 1 Unit of phospholipase D (*Streptomyces* sp, BIOMOL, Plymouth Meeting, Pa., U.S.A). It was left to react for about 15 hours at about 40° C. on a shaker. Once the reaction was complete, the vial was unloaded with about 10 mL of a mixture of chloroform/methanol 2/1 (v/v) and 1 mL of water. The two separated phases were formed, and alkyl PS product was in the down-phase. Alkyl PS remaining in the up-phase was re-extracted with chloroform. After drying the combined two organic phases, silica chromatography (using a 150 mL-column) was used to purify the PS, as described in Example 5. The product was eluted with a mixture of chloroform/methanol (55/45).

About 1 mL of acetate buffer (0.2M; pH 5.5), containing about 40 mM of calcium chloride and about 200 mg of ethanolamine were prepared in a 20-mL disposable vial at room temperature, and then pH of the solution was adjusted to the pH of about 5.5 with glacial acetic acid. About 15 mg of 1-O-alkyl-DHA-PC species mixture were added. The vial was generally fully filled with argon. The enzymatic reaction was started by adding about 1 unit of phospholipase D (*Streptomyces* sp, BIOMOL, Plymouth Meeting, Pa., USA). It was left to react for about 15 hours at about 40° C. on a shaker. Once the reaction was complete, the vial was unloaded with about 10 mL of a mixture of chloroform/methanol 2/1 (v/v) and one mL of water. The two separated phases were formed, and alkyl PE is in the down-phase. Alkyl PE remaining in the up-phase was re-extracted with chloroform. After drying the combined two organic phases, silica chromatography was used to purify PE, as described in Example 5. The product was eluted with a mixture of chloroform/methanol 70/30 (v/v). The structures of the two mixtures are shown as below. The molecular species were identified by negative-ion electrospray mass spectrometry.

Example 10

Structural Identification of Alkyl Bond in Ether Phospholipid Species from the Shark Liver, Unusual DHA-Phospholipid Species and Sn-2-DHA-Lysophospholipid Species Acid hydrolysis was performed by treating approximately 1 mg of 1-O-alkyl-2-hydroxy-PC species mixture with about 1 mL of 0.012 M hydrochloric acid in methanol and about 0.5 mL of chloroform for about 20 min at room temperature. A control sample was also made by treating approximately 1 mg of 1-O-alkyl-2-hydroxy-PC species mixture with about 1 mL of water in methanol and about 0.5 mL of chloroform for about 20 min at room temperature. After extraction of the lipids in the two solutions, the lipid species were analyzed by positive-ion electrospray mass spectrometry. It has been found that the percentage of five alkyl Lyso PC molecular species in the control sample are almost identical to that of the alkyl Lyso PC species in the samples treated with hydrochloric acid. It indicated that ether lipid fatty chains, linked to the sn-1 position, in mixtures of ether phospholipid species are 1-O-alkyl linkage, rather than 1-alk-1'-enyl linkage (plasmalogen species).

Figure 3:
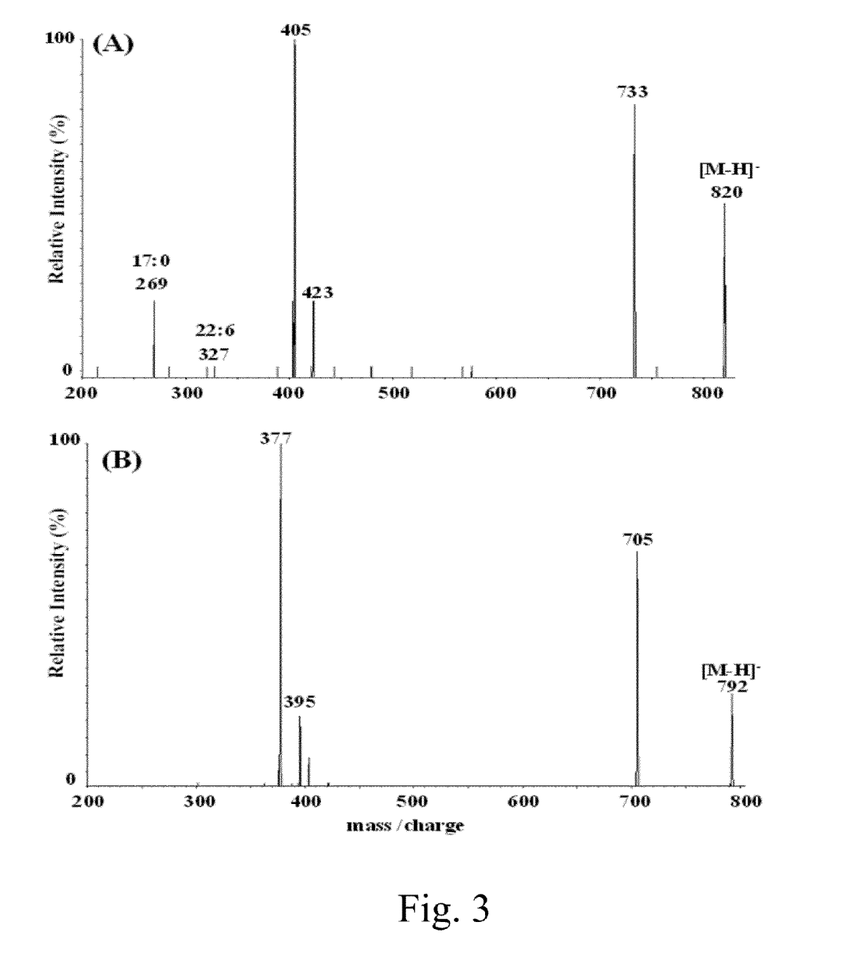
FIG. 3 is a CID product ion spectra of deprotonated molecules of sn-1-17:0-sn-2-DHA PS species (A); and 1-O-16:0-sn-2-DHA PS species (B)

The PC molecular species from the liver of the fishes were identified by collision-induced-dissociation (CID) of deprotonated molecules of transphosphatidylated fish liver-PS because the fatty chains linked to the sn-1 and sn-2 positions in mixtures of transphosphatidylated-PS and -PE species are almost identical to those of the PC species mixtures after the transphos-phatidylation. Structures of unusual molecular species in the liver of saltwater fishes, such as sn-1-17:0-sn-2-DHA PC species and 1-O-16:0-sn-2-DHA PC species, have been identified by electrospray ionization CID of deprotonated molecules of transphosphatidylated fish liver-PS species using published methods. Refer to FIGS. 3(A) and 3(B), where FIG. 3 (A) is the CID product ion spectra of deprotonated molecules of sn-1-17:0-sn-2-DHA PS species; and FIG. 3(B) is the CID product ion spectra of deprotonated molecules of 1-O-16:0-sn-2-DHA PS species. The gas-phase ion chemistry of the phospholipid species have been described in details in the papers [Chen, Tandem mass spectrometric approach for analyzing the molecular species aminophospholipids, *Lipids*, 28, 85 (1997); Chen et, al. *Biomed. Mass Spectrom.* 21, 655 (1992); Chen and Claeys, Characterization of ω-3-docosahexaenoic acid-containing molecular species of phospholipids in rainbow trout liver, *J. Agr. Food Chem.* 42, 3210 (1996)].

Figure 4:
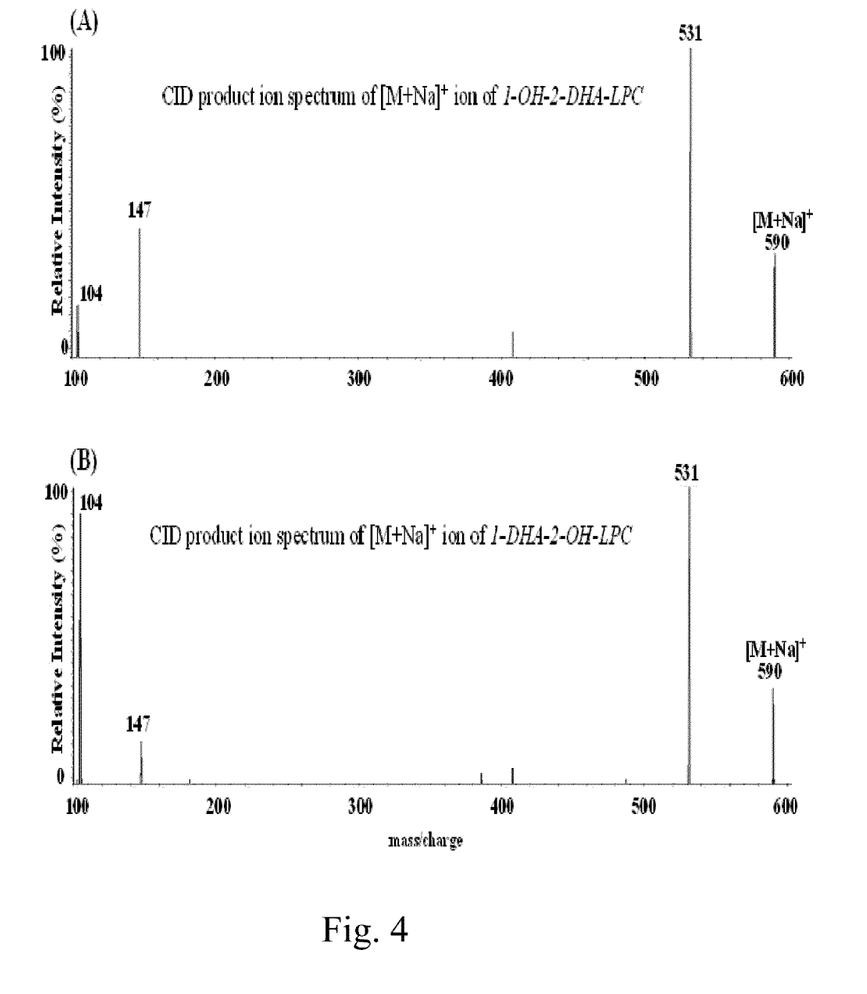
FIG. 4 is a CID product ion mass spectra of sn-1-OH-sn-2-DHA LPC (A) and sn-1-DHA-sn-2-OH LPC (B).

The difference in chemical structures of sn-1-DHA-sn-2-OH-Lyso PC and sn-1-OH-sn-2-DHA-Lyso PC in the species mixtures (from shark liver) were identified by CID of [M+Na]$^+$ adduct ions of the species, based on the published method [Han and Gross, Structural determination of lysophospholipid regioisomers by electrospray ionization tandem mass spectrometry, *J. Am. Chem. Soc.*, 118, 451 (1996)]. The peak intensity ratio of product ions 147/104, generated by CID of sodiated sn-1-OH-sn-2-DHA Lyso PC species (see FIG. 4(A) which is a CID product ion mass spectra of sn-1-OH-sn-2-DHA LPC), is greater than that of product ions 147/104, generated by electrospray ionization CID of sodiated sn-1-DHA-sn-2-OH Lyso PC species (see FIG. 4(B) which is a CID product ion mass spectra of sn-1-DHA-sn-2-OH LPC).

A PE SCIEX (Toronto, Canada) API 3000 triple-quadrupole tandem mass spectrometer equipped is performed using a triple-quadrupole tandem mass spectrometer equipped with a Turbo Ionspray interface of electrospray ionization. For the analyses of Lyso PC isomers, all samples are dissolved in 1:1:0.01 chloroform/methanol/NaCl (1M), and infused directly into the mass spectrometer using a syringe pump as described in the reference paper; for the analyses of PC, PE and PC mixtures, all sample are dissolved in 1:1 chloroform/methanol, and infused directly into the mass spectrometer, as described in the reference papers.

Docosahexaenoic acid (22:6n-3; DHA) is an important fatty acid in prenatal brain development and maintenance of human brain function. DHA deficiency in the brain causes the abnormality of membrane DHA phospholipid species leading to markedly affected neurotransmission, membrane-bound enzyme and ion channel activities [Kim, Novel metabolism of docosahexaenoic acid in neural cells, J. Biol. Chem. 282: 18661 (2007); Lukiw et. al., "A role of docosahexaenoic acid-derived neuroportectin D1 in neural cell survival and Alzheimer's disease", J. Clin. Investigation, 115: 2774 (2005)]. An extraordinary degree of structural specificity of DHA cannot be replaced with those of other polyunsaturated fatty acids, even docosapentaenoic acid (22:5n-6) [Lim et. al., "An extraordinary degree of structural specificity is required in neural phospholipids for optimal brain function: n-6 docosapentaenoic acid substitution for docosahexaenoic acid leads to a loss in spatial task performance", J. Neurochem. 95: 848 (2007)].

DHA cannot be synthesized in the brain, and it has to be supplied entirely from the diet and delivered into the brain by plasma [Spector, "Plasma free fatty acid and lipoproteins as sources of polyunsaturated fatty acid for the brain". J. Mol. Neurosci. 16:159 (2001)]. Although DHA-containing lipid supplements, such as fish and algea oils (mainly consisting of enriched DHA species in triglycerides) have shown benefits in the alleviation of coronary atherosclerosis, it is still questionable whether these DHA molecules can be used as the brain nutrients [Arendash, et. al., "A diet high in omega-3 fatty acids does not improve or protect cognitive performance in Alzheimer's transgenic mice", Neuroscience, 149: 286 (2007); Freund-Levi et. al., ω-3 fatty acid treatment in 174 patients with mild to moderate Alzheimer's disease: Omeg AD study, Arch Neurol. 63: 1402 (2006)]. Unlike other tissues, the brain uptake of DHA needs to overcome the blood-brain barrier.

Studies with whole animals as well as with in vitro systems showed that DHA is transported across the blood-brain barrier more efficiently when they are esterified to lysophospholipid species, which are formed from sn-1-acyl fatty chains/sn-2-DHA phospholipid species [Chen and Subbaiah, "Phospholipid and fatty acid specificity of endothelial lipase: potential role of the enzyme in the delivery of docosahexaenoic Acid (DHA) to tissues", Biochim. Biophys. Acta, 171, 1319 (2007); Lagarde et. al., "Lysophosphatidylcholine as preferred carrier form of docosahexaenoic acid to the brain", J. Mol. Neurosci. 16: 201 (2001); Thies et. al., "Unsaturated fatty acids esterified in 2-acyl-1-lysophosphatidylcholine bound to albumin are more efficiently taken up by the young rat brain than the unesterified form", J. Neurochem. 59:1110 (1992)].

It has been also reported that sn-1-ether fatty chains/sn-2-DHA (mainly sn-1-alkyl fatty chains/sn-2-DHA) phospholipid species may cross through the intestinal barrier easily because the rate of hydrolyzing sn-1-ether fatty chains/sn-2-DHA phospholipids by phospholipases can be significantly slowed down [Paltauf, "Ether lipids in biomembranes". Chem. Phys. Lipids 74: 101 (1994); Chen and Subbaiah, "Phospholipid and fatty acid specificity of endothelial lipase: potential role of the enzyme in the delivery of docosahexaenoic Acid (DHA) to tissues", Biochim. Biophys. Acta, 171: 1319 (2007)], and most of the species are relatively stable in the metabolism with high density lipoprotein (HDL) in vivo, compared with sn-1-acyl fatty chains/sn-2-DHA phospholipid species. A study has shown that brain capillary endothelial cells can bind high-density lipoprotein [Martin-Nizard, et. al., "Interactions of high-density lipoprotein 3 with brain capillary endothelial cells". Biochim. Biophys. Acta 1005: 201 (1989)], while a new route by uptake and transport of high-density lipoprotein to the brain with a vitro blood-brain barrier model has been also reported [Balazs, et. al., "Uptake and transport of high-density lipoprotein (HDL) and HDL-associated α-tocopherol by an in vitro blood-brain barrier model". J. Neurochem. 89: 939 (2004)].

It should be stated here that lysophosphatidylcholine (LysoPC) enriched in DHA could be "a fastest vehicle" for the delivery of DHA to the brain. An early in vivo study has demonstrated that after intravenous injection of labeled sn-1-acyl fatty chains LysoPC-albumin complex to adult squirrel monkeys, the exogenous labeled lipids can reach in the brain just in 20 minutes [Illingworth and Portman, "The uptake and metabolism of plasma lysoPC in vivo by the brain of squirrel monkeys". Biochem. J. 130: 557 (1972)]. About 70% of the injected LysoPC species are taken up in the brain and then are acylated to form PC species. It has been reported that DHA-PC in neurons can be converted to DHA-PS by the PS synthase-1 [Stone and Vance, "Phosphatidylserine-synthase-1 and -2 are located to mitochondria-associated membranes". J. Biol. Chem. 275: 34534 (2000)]. An in vitro experiment has demonstrated that the accumulation of DHA-PS in Neuro-2A cells may protect the neurons from apoptotic death [Kim, H. Y.; Akbar, M.; Lau, A.; Edsall, L. "Inhibition of neuronal apoptosis by docosahexaenoic acid (22:6n-3)". J. Biol. Chem. 275: 35215 (2000)].

From above mentioned results, it is clear to see that phospholipids that contain sn-1-acyl fatty chains/sn-2-docosahexaenoic acid species, sn-1-ether fatty chains/sn-2-docosahexaenoic acid species, and sn-1-docosahexaenoic acid/sn-2-hydroxyl molecules are the important carriers in the delivery of DHA into the brain.

Applicants have prepared the molecular species mixtures of various phospholipids with over 85% purity, which contain enriched both sn-1-acyl fatty chains/sn-2-docosahexaenoic acid molecular species and sn-1-alkyl fatty chains/sn-2-docosahexaenoic acid molecular species.

Applicants have prepared the molecular species mixtures of various phospholipids with over 90% purity, which contain only enriched sn-1-ether fatty chains/sn-2-docosahexaenoic acid molecular species.

Applicants have made the molecular species mixtures of lysophosphatidylcholine with over 85% purity, which contains enriched sn-1-docosahexaenoic acid molecular species.

It should be noted that the terms "first", "second", and "third", and the like may be used herein to modify elements performing similar and/or analogous functions. These modifiers do not imply a spatial, sequential, or hierarchical order to the modified elements unless specifically stated.

While the disclosure has been described with reference to several embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiments disclosed as the best mode contemplated for carrying out this disclosure, but that the disclosure will include all embodiments falling within the scope of the appended claims.

What is claimed is:

1. A process for preparing a mixture of sn-1-docosahexaenoyl/sn-2-hydroxyl molecular species of fish liver lysophosphatidylcholine, the process comprising:
    immediately freezing a fresh fish liver after withdrawing from a saltwater fish;
    fragmenting the frozen fish liver into small fragments;
    extracting crude lipids from the liver fragments by using organic solvents;
    isolating of the crude phospholipids from the extracted lipids by the precipitation of the crude phospholipids in acetone for about 12 to about 15 hours at about −20 C.°; and
    drying the precipitated phospholipids;
    further purifying the fish liver lysophosphatidylcholine to at least about 85% purity from the phospholipids by silica chromatography.

2. The process of claim 1 wherein the said the saltwater fish is selected from the group consisting of: shark, tuna, salmon, monk and common dolphinfish (coryphaena).

3. The process of claim 1 wherein the said the enriched sn-1-docosahexaenoyl/sn-2-hydroxyl molecules of the fish liver lysophosphatidylcholine is in the total molecular species range from about 10% to about 40% by weight.

4. A process for preparing a molecular species mixture of ether phosphatidylcholine that contains sn-1-ether fatty chains/sn-2-docosahexaenoyl molecules, the process comprising:
    immediately freezing a fresh fish liver after withdrawn from a saltwater fish;
    fragmenting the frozen fish liver into small fragments;
    extracting crude lipids from the liver fragments by using organic solvents;
    purifying the phosphatidylcholine to at least 85% purity from the extracted crude lipids by silica chromatography;
    further purifying the sn-1-ether fatty chains/sn-2-hydroxyl lysophosphatidylcholine species to at least 90% purity from the reacted mixture after removing acyl fatty chains in the molecular species of the purified phosphatidylcholine in by the hydrolysis with a basic solution where the pH is greater than about 10;
    acylating the sn-1-ether fatty chains/sn-2-hydroxyl lysophosphatidylcholine species mixture with docosahexaenoic acid into a sn-1-ether fatty chains/sn-2-docosahexaenoyl phosphatidylcholine species mixture; and
    finally purifying the sn-1-ether fatty chains/sn-2-docosahexaenoyl phosphatidylcholine species by silica chromatography.

5. The process of claim 4 where the saltwater fish is selected from the group consisting of: shark, tuna, salmon, monk and common dolphinfish (coryphaena).

6. The process of claim 4, wherein the said the sn-1-ether fatty chains/sn-2-docosahexaenoyl phosphatidylcholine species are over 90% pure by weight.

7. The process of claim 4, wherein the said the sn-1-ether fatty chains contain alkyl or/and alkenyl linkage fatty groups of 14 to 20 carbon atoms.

8. A process for the preparation of a chemical composition of a molecular species mixture of the sn-1-ether fatty chains/sn-2-docosahexaenoyl phosphatidylethanolamine, purified to at least 90% purity through chromatography purification, the process comprising:
    immediately freezing a fresh fish liver after withdrawing it from a saltwater fish;
    fragmenting the frozen fish liver into small fragments;
    extracting the crude lipids from the liver fragments by using organic solvents;
    purifying the phosphatidylcholine to at least 85% purity from the extracted crude lipids by silica chromatography;
    purifying the sn-1-ether fatty chains/sn-2-hydroxyl lysophosphatidylcholine species to at least 90% purity from the reacted mixture after removing acyl fatty chains in the molecular species of the purified phosphatidylcholine by the hydrolysis with a basic solution at a pH of greater than about 10;
    acylating the sn-1-ether fatty chains/sn-2-hydroxyl lysophosphatidylcholine species mixture with docosahexaenoic acid into a sn-1-alkyl ether fatty chains/sn-2-docosahexaenoyl phosphatidylcholine species mixture;
    purifying the sn-1-ether fatty chains/sn-2-docosahexaenoyl phosphatidylcholine species by silica chromatography;
    transphosphatidylating a mixture of the sn-1-ether fatty chains/sn-2-docosahexaenoyl phosphatidylcholine species into a mixture of the sn-1-ether fatty chains/sn-2-docosahexaenoyl phosphatidylethanolamine species; and
    finally purifying the sn-1-ether fatty chains/sn-2-docosahexaenoyl phosphatidylethanolamine species by silica chromatography.

9. The process of claim 8 wherein the saltwater fish is selected from the group consisting of: shark, tuna, salmon, monk and common dolphinfish (coryphaena).

10. The process of claim 8, wherein the said the sn-1-ether fatty chains/sn-2-docosahexaenoyl phosphatidylethanolamine species are over 90% pure by weight.

11. The of claim 8, wherein the said the sn-1-ether fatty chains contain alkyl or/and alkenyl linkage fatty groups of 14 to 20 carbon atoms.

12. A process for the preparation of a chemical composition of a molecular species mixture of the sn-1-ether fatty chains/sn-2-docosahexaenoyl phosphatidylserine, purified to at least 90% purity through chromatography purification, the process comprising:
    immediately freezing a fresh fish liver after being withdrawn from a saltwater fish;
    fragmenting the frozen fish liver into small fragments;
    extracting the crude lipids from the liver fragments by using organic solvents;
    purifying the phosphatidylcholine to at least 85% purity from the extracted crude lipids by silica chromatography;
    further purifying the sn-1-ether fatty chains/sn-2-hydroxyl lysophosphatidylcholine species mixture to at least 90% purity from the reacted mixture after removing acyl fatty chains in the molecular species of the purified phosphatidylcholine by hydrolysis with a basic solution at a pH of greater than about 10; acylating the sn-1-ether fatty chains/sn-2-hydroxyl lysophosphatidylcholine species mixture with docosahexaenoic acid into a sn-1-ether fatty chains/sn-2-docosahexaenoyl phosphatidylcholine species mixture;

purifying the sn-1-ether fatty chains/sn-2-docosahexaenoyl phosphatidylcholine species with silica chromatography; transphosphatidylating a mixture of the sn-1-ether fatty chains/sn-2-docosahexaenoyl phosphatidylcholine species into a mixture of the sn-1-ether fatty chains/sn-2-docosahexaenoyl phosphatidylserine species; and finally purifying the sn-1-ether fatty chains/sn-2-docosahexaenoyl phosphatidylserine species by silica chromatography.

13. The process of claim 12 wherein the saltwater fish is selected from the group consisting of: shark, tuna, salmon, monk and common dolphinfish (coryphaena).

14. The process of claim 12, wherein the said the sn-1-ether fatty chains/sn-2-docosahexaenoyl phosphatidylserine species are over 90% pure by weight.

15. The process of claim 12, wherein the said the sn-1-ether fatty chains contain alkyl or/and alkenyl linkage fatty groups of 14 to 20 carbon atoms.

* * * * *